United States Patent [19]

Armitage

[11] 4,285,346

[45] Aug. 25, 1981

[54] ELECTRODE SYSTEM

[75] Inventor: David Armitage, Bangor, Wales

[73] Assignee: Harry V. LeVeen, Charleston, S.C.

[21] Appl. No.: 20,355

[22] Filed: Mar. 14, 1979

[51] Int. Cl.³ ............................................. A61N 1/40
[52] U.S. Cl. ..................................... 128/422; 128/804
[58] Field of Search ........... 128/419 R, 420 R, 420 A, 128/421, 422, 423 R, 783, 804, 1.3–1.5

[56] References Cited

U.S. PATENT DOCUMENTS

| | | | |
|---|---|---|---|
| 3,800,802 | 4/1974 | Berry et al. | 128/804 |
| 3,991,770 | 11/1976 | LeVeen | 128/804 |
| 4,095,602 | 6/1978 | LeVeen | 128/804 |
| 4,121,592 | 10/1978 | Whalley | 128/804 |

FOREIGN PATENT DOCUMENTS

| | | | |
|---|---|---|---|
| 2222844 | 11/1973 | Fed. Rep. of Germany | 128/420 |
| 2815156 | 10/1978 | Fed. Rep. of Germany | 128/804 |
| 594895 | 11/1947 | United Kingdom | 128/422 |

*Primary Examiner*—Lee S. Cohen
*Attorney, Agent, or Firm*—Brooks, Haidt, Haffner & Delahunty

[57] ABSTRACT

A pair of electrodes are energized in opposite phase by a radio frequency electric source having a common connection to said electrodes differing in length by a ½ wave length, and electrode isolation when unenergized is obtained utilizing lengths of connecting cable from such common connection which are odd multiples of a ¼ wave length, grounding the common connection.

8 Claims, 4 Drawing Figures

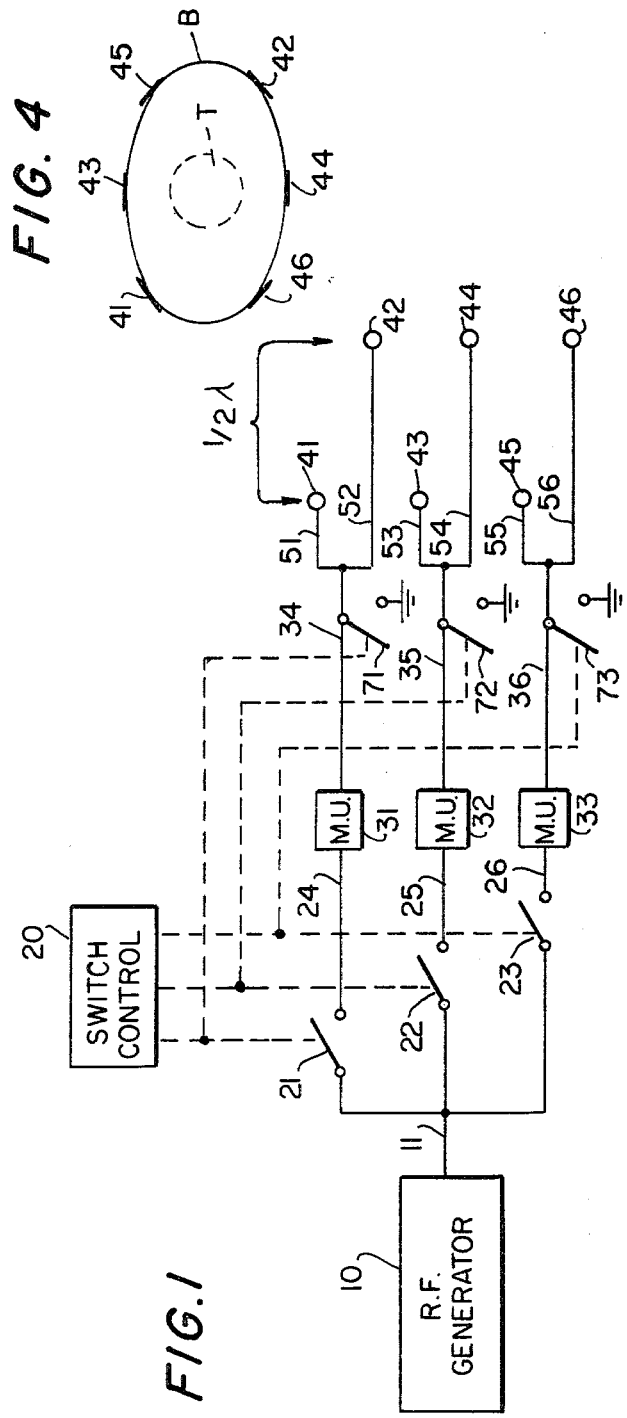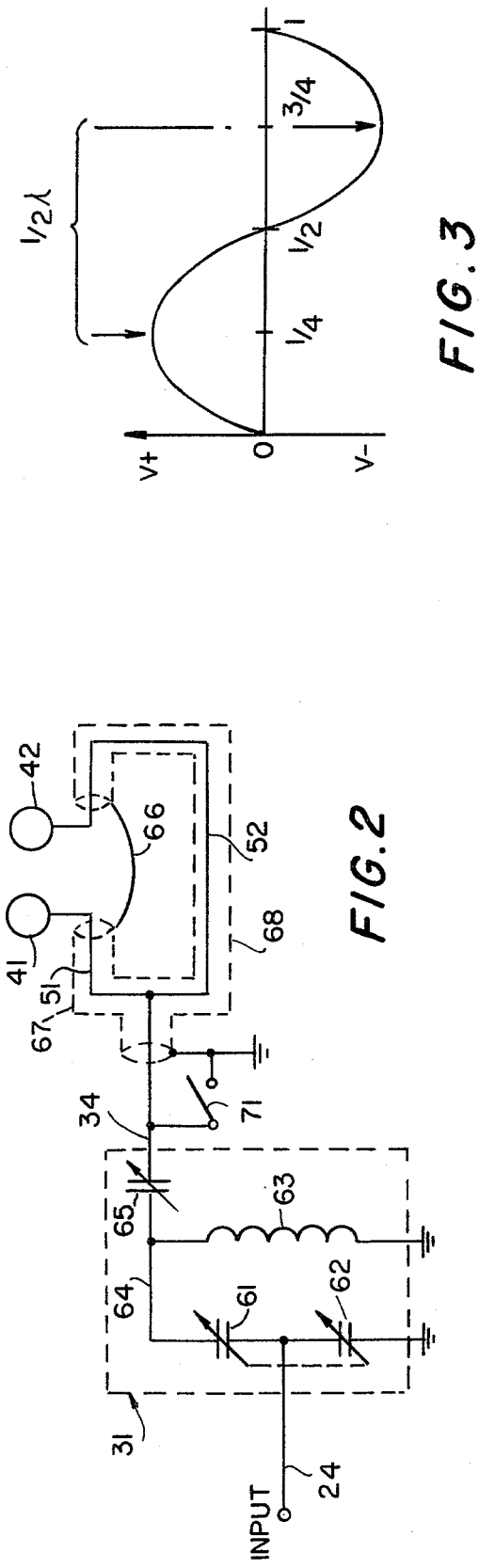

ELECTRODE SYSTEM

This invention relates to local hyperthermia and in particular provides a short wave diathermy apparatus suitable for energizing a pair of applicator electrodes which are applied on opposite sides of the portion of the body to be heated.

Recently it has been found that short wave diathermy(thermotherapy) can be utilized in the treatment of tumors (LeVeen U.S. Pat. No. 3,991,770). This treatment is predicated on the perception that blood flow in tumors is poor, and hence the tumor can be selectively heated to the point of destruction by utilizing relatively high power short wave diathermy without damage to adjacent normal tissue, as the blood flow through the adjacent normal tissue cools at faster rate than the slower blood flow through the tumor. It is also been found that the selectivity obtained can be increased and heating of the subcutaneous layer of skin can be minimized utilizing a multi-portal technique in which pairs of electrodes are positioned at different locations such that, however, the energy paths cross at the location of the tumor. (LeVeen U.S. Pat. No. 4,095,602). In these prior arrangements it has generally been the practice to have one electrode of any pair operating together connected to the hot side of the radio frequency generator employed and the other connected to ground. This has particularly been the case in the multi-portal technique. In the multi-portal technique it has also been the practice to switch from one pair of electrodes to another rather than to energize all simultaneously.

It has subsequently been found that the hot electrode has no respect as to which electrode is grounded, and consequently the desired cross-firing technique is frequently not obtained, particularly when switching from one pair of electrodes to another, so that at any one time only one electrode pair is energized. Thus when three pairs of electrodes have been utilized the one energized hot electrode sees three grounds. In addition it is usually necessary to ground the operating table utilized in any treatment with short wave diathermy and the table itself thus presents another path for leakage to ground.

It is consequently preferable to have each of any pair of associated electrodes at opposite potentials that is one electrode is positive when the other is negative, and vice versa. This can be accomplished by using a phase-splitting transformer but such usage introduces new problems. If more than one pair of electrodes is utilized, the electrodes not being energized must remain free floating at all times.

In accordance with this invention two associated electrodes are kept 180° out of phase by commonly tying them to the output of a radio frequency electric generator through connecting lines which differ in length by an odd number, preferably one, of half wave lengths of the radio frequency output of the generator. In another aspect of this invention isolation of unused electrodes is obtained by grounding the output of the radio frequency generator at its common connection to the pair of electrodes and by making the lengths of the lines connecting the output of the radio frequency generator to the electrodes an odd number of quarter wave lengths. Thus in the preferred case one electrode is a quarter wave length from a common connection to the radio frequency generator and the other electrode is three quarters of a wave length from such common connection. In transmission line theory a short circuit appears as an open circuit one quarter of a wave length away, while an open circuit looks like a short circuit. Thus, when any electrode pair is not in use by grounding the output of the generator to such electrodes, the electrodes are electrically free floating and appear to any other energized electrodes as an open circuit when operating at the radio frequency of the generator. This sort of arrangement is not straightforward utilizing a phase splitting transformer.

The common frequencies utilized in radio frequency diathermy in the treatment of tumors and the like, and 13.56 MHz and 27.12 MHz. At 13.56 MHz in accordance with the present invention the cables connecting a pair of electrodes which are associated with a common input will be approximately 3.6 and 10.8 meters and half these lengths at 27.12 MHz (wave lengths in cable are computed by dividing the wave length in air by the square root of the dielectric constant of the cable).

For a more complete understanding of the practical application of this invention, reference is made to the appended drawings in which:

FIG. 1 is a block diagram illustrating an apparatus in accordance with this invention;

FIG. 2 is a schematic diagram illustrating the connections to one associated pair of electrodes shown in FIG. 1;

FIG. 3 is a graph illustrating the principles of this invention; and

FIG. 4 is a schematic diagram showing the placement of electrodes of the apparatus of FIG. 1 in usage.

Referring more particularly to FIG. 1 there is shown an apparatus in accordance with the present invention for sequentially energizing three different associated pairs of electrodes which in usage are commonly associated with the same load, that is, a tumor mass located in a portion of the body. In FIG. 1 the reference numeral 10 designates a radio frequency generator. For the purposes of this invention, generator 10 is entirely conventional and can consist of an ecxiter and a power amplifier capable of sustained operation at 13.56 MHz at any selectable power level up to 2 Kw. The RF output of generator 10 is connected through a line 11 to 3 switches 21, 22, and 23 which for simplicity's sake are shown as single pole, single throw switches, although in practice switching diodes are preferred. Switches 21, 22, and 23 are controlled by a switch control citrcuit 20, which preferably is arranged such that under manual control any of switches 21, 22, and 23 can be closed or under automatic control can be programmed selectively closing each switch one at a time for any period of duration. Switches 21, 22, and 23 are respectively connected through lines 24, 25, and 26 through impedance matching units 31, 32, and 33, respectively, to output lines 34, 35, and 36, respectively. Output lines 34, 35, and 36 are respectively connected to a pair of electrodes 41 and 42, a pair of electrodes 43 and 44 and a pair of electrodes 45 and 46. Electrodes 41–46 are each typically constructed of 4 inch copper disks mounted on insulated handles.

Each electrode disk 41, 43, and 45 is connected through its handle, respectively, to output lines 34, 35, and 36 by connecting lines 51, 53, and 55, which each have a length equal to ¼ of a wave length in the cable at the frequency of 13.56 MHz. Electrodes 42, 44 and 46 are connected through their handles to output lines 34, 35, and 36, respectively, by lines 52, 54, and 56. Each of lines 51, 53 and 55 thus has a common connection with each of lines 52, 54, and 56, respectively, at the connection with each of output lines 34, 35 and 36, respectively. Connecting lines 52, 54 and 56 are, however, in length equal to ¾ of a wave length in the cable at a frequency of 13.56 MHz. Consequently each electrode pair 41-42, 43-44, and 45-46 is electrically ½ wave length apart at the frequency of 13.56 MHz.

Output lines 34, 35 and 36 are also connected, respectively, through single pole, single throw relay operated switches 71, 72 and 73 to ground. Switches 71, 72 and 73 are controlled by switch control circuit 20, such that when each switch 21, 22 and 23 is closed, each switch 71, 72, and 73 respectively, is open and vice versa. Thus, when any electrode pair, such as electrodes 41 and 42, is activated, and electrode pairs 43-44 and 45-46 are deactivated by closure of switch 21 and opening of switches 22 and 23, respectively, switch 71 is open and switches 72 and 73 are closed, thus electrically floating electrodes 43, 44, 45 and 46, Because connecting lines 53, 54, 55 and 56 are odd multiples of ¼ wave length however, electrodes 43, 44, 45, and 46 appear to be open circuits at the frequency at 13.56 MHz to electrodes 41 and 42.

FIG. 2 shows in more detail the construction of matching unit 31 and connections to electrodes 41 and 42 which are typical for the other associated pairs of electrodes 43-44 and 45-46 and their associated matching units 32 and 33.

As can be seen in FIG. 2 matching unit 31 has its input line 24 from switch 21 connected to the center of a pair of ganged variable capacitors 61 and 62. Line 24 is connected through capacitor 62 to ground and through capacitor 61 to line 64 connected to a coil 63 leading to ground and to a capacitor 65 leading to output line 34.

As can also be seen in FIG. 2 connecting line 51 is the central conductor of a coaxial cable and is connected to the copper disk electrode 41, and line 52 is the central conductor of a coaxial cable and is connected to electrode disk 42. Conductors 51 and 52 have coaxial sheaths 67 and 68 connected together at their common termination with output line 34 and are connected to ground at that point. The connection of switch 71 to ground is preferably made as close to that point as possible. The outer conductors 67 and 68 of lines 51 and 52 are also interconnected at their ends adjacent electrodes 41 and 42 by a line indicated by the reference number 66.

FIG. 3 shows a plot of voltage, as the ordinate, against distance, as the abssissa, along the length of the cable equal to one wave length of a radio frequency signal applied to one end of the cable taken at the instant the applied voltage passes through zero. As can be seen at that instant the voltage one quarter of a wave length along the cable reaches a maximum and the voltage three quarters of a wave length along the cable reaches a minimum; thus the separation between the maximum and the minimum voltage is a ½ wave length.

Referring to FIG. 4, in practice electrodes 41-46 are positioned adjacent a surface of a body B having a tumor mass T such that associated pairs of electrodes, such as 41 and 42, are disposed on opposite sides of the tumor mass T. The RF generator is then energized and the switch controls are operated to close switches 21, 22, and 23 in whatever desired sequence is selected. The voltage standing wave ratios in lines 24, 25, and 26 are measured as these lines are energized and impedance matching units 31, 32, and 33 are adjusted to minimise such ratio, i.e., maximize the quotient of forward voltage to reflected voltage. This is done first by adjusting ganged capacitors 61 and 62 for maximum ratio, and then adjusting capacitor 65 for a maximum ratio, and repeating the process until no further improvement can be obtained.

I claim:

1. An apparatus for developing a radio frequency voltage between a pair of electrodes whereby a radio frequency electro-magnetic field can be applied to a load between said electrodes comprising generator means for generating radio frequency electrical energy having an output at which a voltage varying at a radio frequency is present, a pair of applicator electrodes, a first electrical line connected at one end thereof to one of said electrodes, a second electrical line connected at one end thereof to the other of said electrodes, said first and second lines being connected at the other ends thereof commonly to said output, and said first line having a length which is an odd number of half wave lengths at said radio frequency longer than said second line.

2. An apparatus according to claim 1 in which said first line is one half wave length longer than said second line.

3. An apparatus according to claim 2 in which the length of said first line is three quarters of a wave length whereby the length of said second line is one quarter length.

4. An apparatus according to claim 1 or claim 2 in which said first and second electrical lines are the central conductors of coaxial cables having outer coaxial conductors commonly connected to ground at the ends thereof adjacent to said output, and having connecting means interconnecting the ends of said outer conductors at the ends thereof adjacent said electrodes.

5. An apparatus for developing a radio frequency voltage selectively between any single pair of a plurality of electrodes associated with a common load whereby the remaining electrodes are floated disassociated from the selected pair of electrodes which comprises generator means for generating radio frequency electrical energy having an output at which a voltage varying at a radio frequency is present, switching means having a plurality of switch outputs connected to said output of said generator means for selectively coupling said generator means output to any one of said plurality of switch outputs, a plurality of associated pairs of applicator electrodes, a plurality of electrical lines, each electrical line being connected to a said electrode and the pair of electrical lines connected to each associated pair of electrodes being connected to a said switch output of said switching means, means for grounding each said electrical line located a distance equal to an odd number of quarter wave lengths from the connection of each such line to the electrode to which such line is connected, and means for actuating said grounding means when the switch output to which such grounding means is connected is not coupled by said switching means to said generator means output whereby said electrodes connected thereto are at ground potential but appear as open circuits at said radio frequency.

6. An apparatus according to claim 5 in which the electrical lines connected to a given associated pair of electrodes are commonly connected to the said switch output associated therewith and in which the length of the electrical line connected to one of said given associated pair of electrodes is an odd number of half wave lengths at said radio frequency longer than the length of the other electrical line connected to the other of said given associated pair of electrodes.

7. Apparatus according to claim 6 in which the length of said one electrical line is one quarter of a wave length and the length of said other electrical line is three quarters of a wave length.

8. Apparatus according to claim 5, 6, or 7 in which said electrical lines connected to a given associated pair of electrodes are the central conductors of coaxial cables having outer coaxial conductors commonly connected to ground at the ends thereof adjacent the said switch output and the said grounding means associated therewith, and connecting means interconnecting the ends of said outer coaxial conductors adjacent said given pair electrodes.

* * * * *